US006963822B1

(12) United States Patent
Nakazato

(10) Patent No.: US 6,963,822 B1
(45) Date of Patent: Nov. 8, 2005

(54) METHOD AND APPARATUS FOR SEPARATION, ANALYSIS AND EVALUATION OF DATA

(75) Inventor: Tokiya Nakazato, Saitama (JP)

(73) Assignee: K.K. Helena Kenkyujo, Saitama (JP)

( * ) Notice: Subject to any disclaimer, the term of this patent is extended or adjusted under 35 U.S.C. 154(b) by 0 days.

(21) Appl. No.: 09/249,131

(22) Filed: Feb. 12, 1999

(30) Foreign Application Priority Data

Feb. 18, 1998 (JP) .......................................... 10-036281

(51) Int. Cl.[7] .............................................. G01N 33/50
(52) U.S. Cl. ....................................... 702/194; 702/21
(58) Field of Search ............................... 702/194, 19–32

(56) References Cited

U.S. PATENT DOCUMENTS

| | | | | | |
|---|---|---|---|---|---|
| 3,784,789 | A | * | 1/1974 | Broek ........................ 708/823 |
| 3,814,255 | A | * | 6/1974 | Smernoff .................... 210/656 |
| 3,894,844 | A | * | 7/1975 | Pinto et al. .................. 436/71 |
| 4,118,781 | A | * | 10/1978 | Brezinski et al. ........... 356/444 |
| 4,420,384 | A | * | 12/1983 | Fujiwara ..................... 204/450 |
| 4,592,089 | A | * | 5/1986 | Hartman ..................... 382/129 |
| 4,920,498 | A | * | 4/1990 | Kaneko ....................... 204/546 |
| 5,580,747 | A | * | 12/1996 | Shultz et al. ................ 435/24 |
| 5,675,760 | A | * | 10/1997 | Houwen et al. ............ 345/440 |
| 5,846,717 | A | * | 12/1998 | Brow et al. .................... 435/6 |
| 5,853,979 | A | * | 12/1998 | Green et al. ................... 435/5 |
| 5,865,975 | A | * | 2/1999 | Bishop ....................... 204/618 |
| 5,904,822 | A | * | 5/1999 | Casavant .................... 204/461 |
| 5,922,184 | A | * | 7/1999 | Binder et al. ............... 204/452 |
| 5,958,202 | A | * | 9/1999 | Regnier et al. ............. 204/451 |
| 2003/0064423 | A1 | * | 4/2003 | Gordon et al. ............. 435/7.92 |

FOREIGN PATENT DOCUMENTS

| | | |
|---|---|---|
| JP | 58-210000 A | 12/1983 |
| JP | 61-196154 A | 8/1986 |
| JP | 06094675 A | 4/1994 |
| JP | 06096138 A | 4/1994 |
| JP | 06241986 A | 9/1994 |
| JP | 06273320 A | 9/1994 |
| JP | 08320313 A | 12/1996 |

OTHER PUBLICATIONS

Translation of Office Action dated Feb. 18, 2000.
Partial Translation of Japanese Laid-Open No. Hei 6-241986, Claims 1–2 and paragraph 0023, as cited in Office Action dated Feb. 18, 2000.

* cited by examiner

Primary Examiner—Marc S. Hoff
Assistant Examiner—Anthony Gutierrez
(74) Attorney, Agent, or Firm—DLA Piper Rudnick Gray Cary US LLP

(57) ABSTRACT

Waveform diagrams of cholesterol and triglyceride, for example, obtained by electrophoresis are overlappedly displayed (superimposed). To compare or overlappedly display two waveform diagrams, one unit of absolute concentration is related to one unit of waveform size for normalization. With this method, phenotype classification of lipid can be easily performed. Further, phenotype can also be performed quantitatively and automatically from two waveform diagrams. Thus, a plurality of waveform diagrams of lipid in serum (plasma) obtained by a densitometer or the like can be quantitatively compared.

12 Claims, 20 Drawing Sheets

| patient attribute Rev.3 .90J |
| --- |
| input(I) communication(X) work sheet(W) end(E) help(H) | scanned date  1997-12-11 ▼ examination item

| cholesterol ▼ |
| --- |
| LDH anthozyme |
| ALP anthozyme |
| cholesterol |
| triglyceride |
| AMY anthozyme |
| CK anthozyme |
| ALP separator |
| serum protein fraction |
| after CHO treatment |
| before TG treatment | reexamination
possible

IV type

V type

METHOD AND APPARATUS FOR SEPARATION, ANALYSIS AND EVALUATION OF DATA

CROSS-REFERENCE TO RELATED APPLICATION

This application is based on, and claims priority from, Japanese Application No. 10-36,281, filed Feb. 12, 1998, which is hereby incorporated by reference.

BACKGROUND OF THE INVENTION

The present invention relates to separation of fluids, with subsequent analysis and evaluation. The fluid may be serum (plasma) lipid and may be separated by, liquid chromatography or electrophoresis, including capillary electrophoresis to determine the concentrations of components of the samples. Determination of concentration of components may be obtained with a densitometer. One particular, but non-limiting aspect of the present invention is cholesterol-triglyceride separation and subsequent analysis.

In the separation and analysis of serum lipid, lipid metabolism is analyzed by separation with respect to specific gravity, which is now an important examination for the treatment of hyperlipemia Serum lipid, when separated with respect to specific gravity by a centrifuge, can be separated into HDL (high-density lipoprotein), LDL (low-density lipoprotein, IDL (intermediate density lipoprotein), VLDL (very low-density lipoprotein), and CM (chylomicron). Since the separation is carried out by an ultracentrifuge, for finer and detailed separation to grasp conditions during separation, this method is difficult to be employed in-the clinical area because it requires much labor and time. Since separation of serum lipid by electrophoresis shows a good correlation with that of an ultracentrifuge and the separation condition can be visually obtained, the electrophoretic lipoprotein separation is employed in routine examination.

In the basic structure of lipoprotein, a core part is formed of triglyceride and cholesterol ester, which is covered with a single layer of film composed of phospholipid and free cholesterol, and a single to several types of apoprotein are attached to the surface. That is, cholesterol and triglyceride and phospholipid of α(HDL) of lipoprotein fraction, pre β(VLDL), between pre and β(IDL), β(LDL), and chylomicron part can be measured to determine ratios of components in the respective fractions. Since metabolism of lipid relative to enzyme and cholesterol transfer protein, and lipoprotein is slightly changed in particle size with the content of triglyceride, close examination of these conditions serves to detect an abnormality of metabolism.

In electrophoresis, lipid is separated into a position a (HDL), pre β position (VLDL), β(LDL), sample application position (chylomicron), and between pre β and β(IDL), and dyed with fat red 7B and the like for measurement. WHO classifies hyperlipemia into six phenotypes of I, IIa, IIb, III, IV, and V. However, in the prior art method where this classification is performed for lipoprotein fraction, total cholesterol value, total triglyceride value, and presence of chylomicron, by visual examination of a serum sample kept in a refrigerator for 12 hours, there have been problems in that the method takes much time, some samples are very difficult to evaluate, since visual examination calls for judgment, and classification is difficult even for skilled persons.

Phenotype classification of hyperlipemia is performed for pre β(VLDL+IDL), β(LDL) and change in chylomicron content, and pre β(VLDL+IDL) is mainly of triglyceride rich, whereas (LDL) is cholesterol rich. Chylomicron, since most of it is triglyceride, in general the phenotype of hyperlipemia is determined from the total triglyceride value (described in fraction name of ultracentrifugal method). That is, VLDL+IDL is determined from the total triglyceride value, and LDL from the total cholesterol value. The presence of chylomicron is determined by visual examination of serum stored in a refrigerator for 12 hours. In the WHO classification, the determination is made as follows.

a. In type I, VLDL+IDL and LDL are normal, whereas only chylomicron is-high.

b. In type IIa, only LDL is high, whereas VLDL+IDL and chylomicron are normal.

c. In type IIb, VLDL+IDL and LDL are high, whereas chylomicron is normal.

d. In type III, VLDL+IDL and LDL approach each other to form broad $E\acute{E}_i$ in the lipoprotein fraction, and determination is impossible without lipoprotein fractionation.

e. In type IV, VLDL+IDL is high, whereas LDL and chylomicron are normal.

f. In type V, chylomicron and VLDL+IDL are high, whereas LDL is normal. To perform such classification, in general, a visual judgment is made with reference to a guideline for hyperlipemia of the Society of Arteriosclerosis. However, since, with the above-described method, lipoprotein fraction can be determined only in ratio, and chylomicron is qualitatively analyzed, it is difficult to make judgment of phenotype automatically. Further, in some analytes, VLDL+IDL contains a large amount of cholesterol, LDL contains a large amount of triglyceride, and such abnormal analytes cannot be detected by the above classification.

SUMMARY OF THE INVENTION

When phenotype classification of hyperlipemia is performed with cholesterol fraction value and triglyceride fraction value, and total concentrations of cholesterol and triglyceride, judgment can be reasonably performed without performing visual examination of serum or lipoprotein fractionation which are performed for chylomicron, and can be judged by the computer. Further, with this method is possible to find an abnormal analyte which could not be found by conventional classification, which is useful for diagnosis of metabolic error and for observation of treatment method and treatment effect.

It is therefore an object of the present invention to make classification of phenotype of hyperlipemia possible to be judged from examination result.

In accordance with the present invention which attains the above object, there is provided a method an apparatus for performing separation, analysis and examination of lipid in blood in which a predetermined sample obtained by electrophoresis is scanned to obtain a waveform and the waveform is processed, characterized by means for integration (or, alternatively, the step of integrating) each waveform obtained by scanning; means for normalizing (or alternatively the step of normalizing) the waveform from integrated value of waveform obtained by integration and an absolute amount of the sample; means for storing (or alternatively the step of storing) a plurality of normalized waveforms, and means for simultaneously outputting (or, alternatively, the step of simultaneously outputting) a plurality of stored waveforms. In the examination data processing apparatus according to the present invention, by simultaneously outputting a plurality of normalized waveforms, understanding of lipid analysis, for example, classification of phenotype and the like can be performed more simply.

In one non-limiting example, the means for simultaneously outputting (and the step of simultaneously outputting) a plurality of waveforms may multiply the plurality of waveforms by a same coefficient and output them to different locations, or may output overlapped (i.e., superimposed) waveforms to a same location. In particular, by overlapped outputting, understanding the feature of phenotype classification is simplified.

The simultaneously outputted waveforms may be those of time series of a same analyte and of a same examination item, or those of different examination items of a same analyte. These are outputted according to the purpose. When using examination results by a plurality of waveforms of different examination items of a same analyte, judgment of phenotype of lipid can be performed automatically. These examination results of a plurality of waveforms may only be those for cholesterol and triglyceride. Since the phenotype classification is performed automatically, diagnosis and the like can be made without human judgment.

A recording medium storing a program for achieving the above function by a computer also falls within the scope of the present invention.

BRIEF DESCRIPTION OF THE DRAWINGS

The foregoing objects and advantages of the present invention, together with other objects and advantages which may be attained by its use, will become more apparent upon reading the following detailed description of the invention in conjunction with the drawings.

In the drawings:

FIG. 2, comprising

FIG. 4A and FIG. 4B, are an enlarged diagrams showing parts of the electrophoretic bath of FIG. 3;

FIG. 8 is a diagram showing a display for setting an examination item;

FIG. 10, comprising

FIG. 16, comprising

FIG. 17, comprising

FIG. 18, comprising

DETAILED DESCRIPTION OF THE INVENTION

Figure 1:
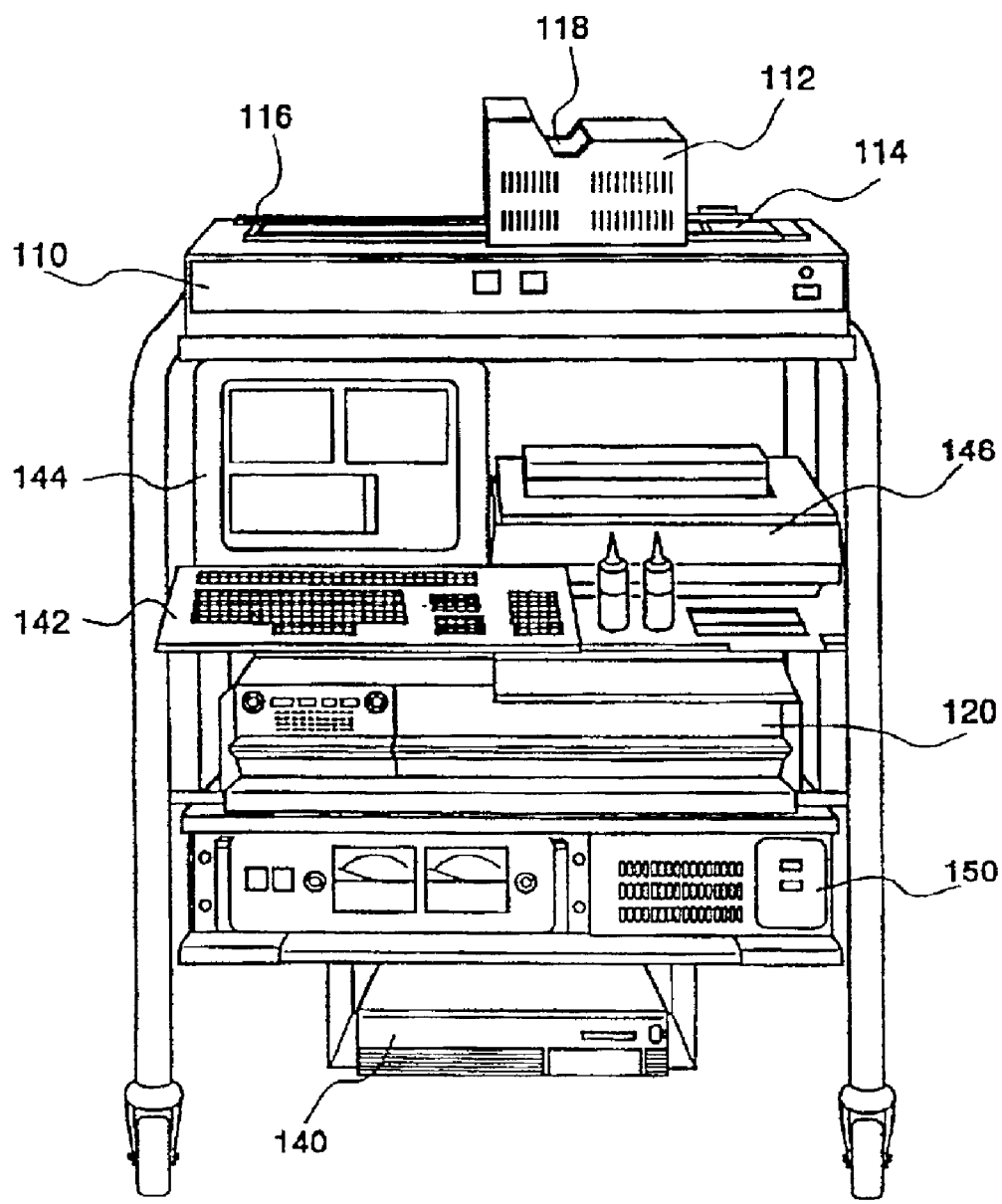
FIG. 1 is a diagram showing an electrophoretic apparatus and an evaluation device such as a densitometer.

With reference to the drawings, FIG. 1 shows an automatic electrophoretic apparatus, a densitometer and a computer system which are used, for example, in lipid analysis. In FIG. 1, an electrophoretic apparatus 110 has a sample applicator 112, a sample table 114, an electrophoretic bath 116, and a reagent vial rack 118. A densitometer 120 is connected to the computer system which performs processing and control of the densitometer 120. The computer system comprises, as is conventional, a computer main unit or CPU 140, a keyboard 142, a display (CRT) 144, a printer 146, and may include other peripheral devices. A power supply 150 provides electric power to the entire apparatus of FIG. 1.

Figure 2A:
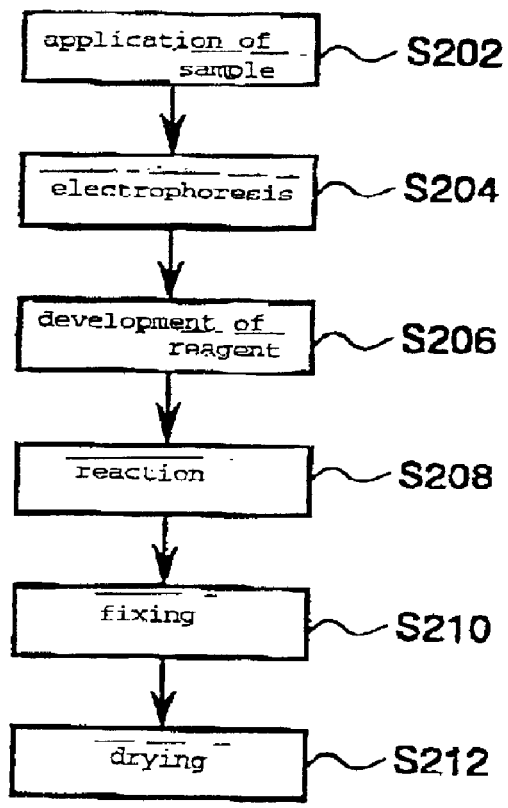
FIG. 2A and FIG. 2B, is a flow chart showing, diagrammatically, an electrophoretic separation method (FIG. 2A) and, diagrammatically, the result of a separated and visualized sample (FIG. 2B)

FIG. 2, and particularly FIG. 2A is a flow chart showing a steps in the electrophoresis process.

Figure 3:
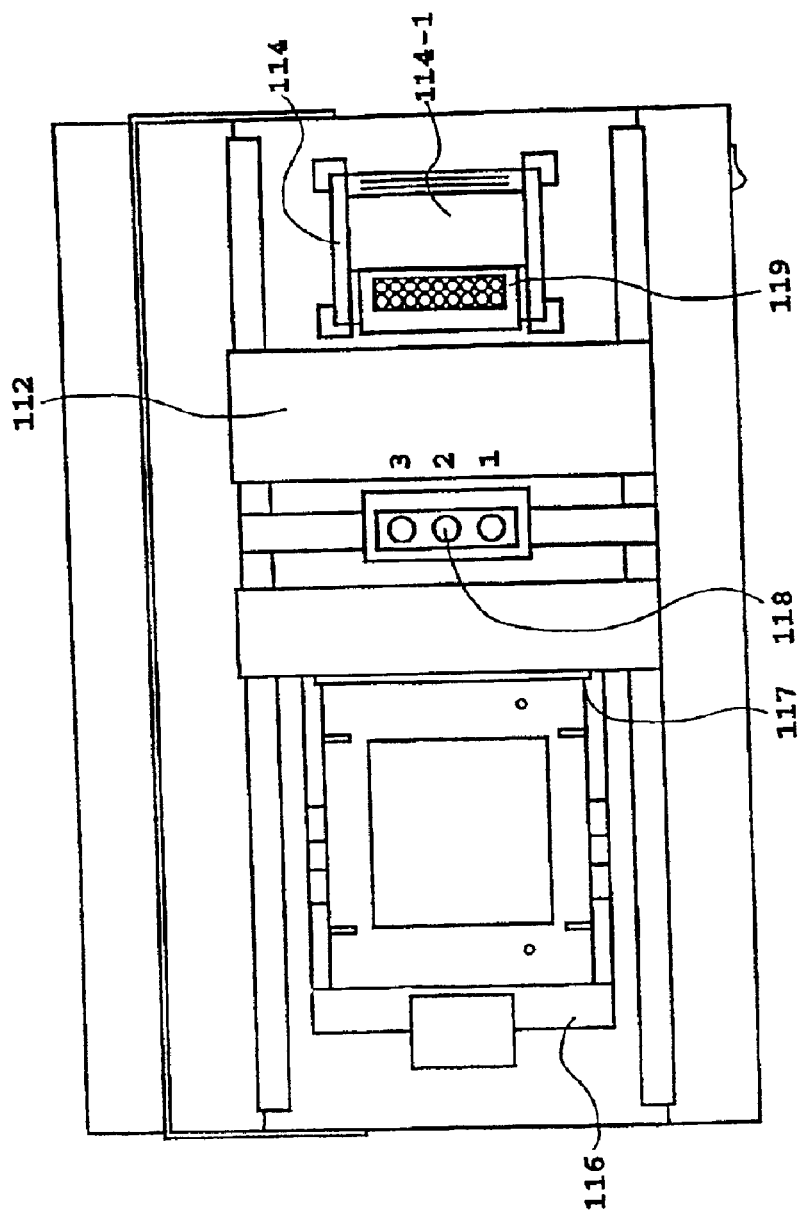
FIG. 3 is a diagram showing an electrophoretic bath as viewed from the upper side.
Figure 4:
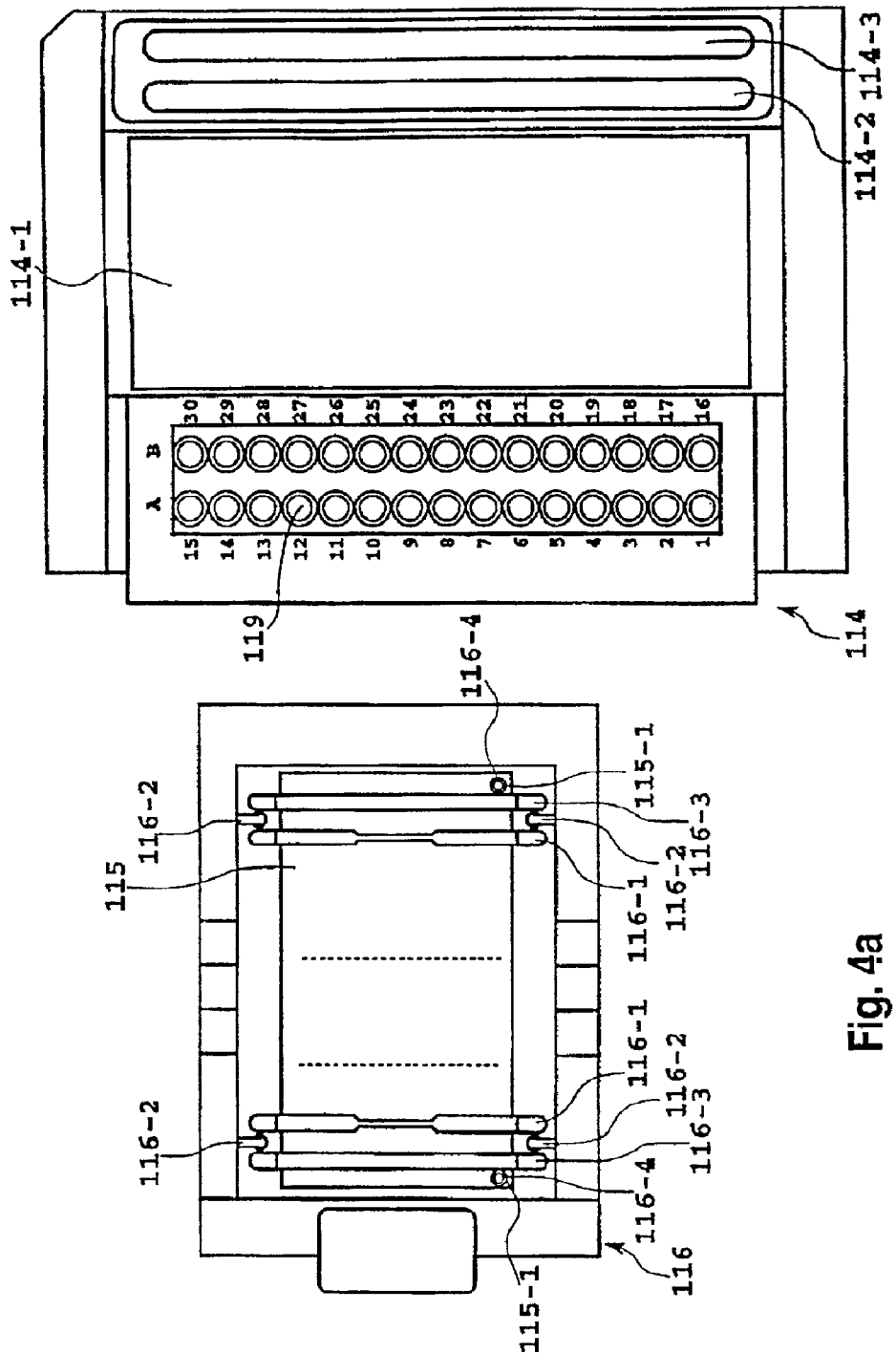
FIG. 4, comprising

FIG. 3 is a diagram of the electrophoretic apparatus 110 shown in FIG. 1 as viewed from the upper side and the apparatus includes a slide cover 117. FIGS. 4A and 4B are enlarged diagrams showing the sample table 114 and the electrophoretic bath 116, respectively, of the electrophoretic apparatus of FIG. 3. The procedure or method of electrophoresis, such as in lipid analysis, as performed using the aforementioned apparatus, 1 will be described with reference to the flow chart of FIG. 2A, FIG. 3, FIG. 4A and FIG. 4B First, preparation is made for performing electrophoresis. A thin agarose film 115 is used as the medium for electrophoresis and is placed in the electrophoretic bath 116 in FIG. 4A. The agarose film includes two pin holes or alignment apertures 115-1 through which are inserted set pins 1164. A reagent developing rod 116-1 having magnetic materials at both ends and an electrode rod 116-3 are placed to be attracted to the magnetic electrode 116-2 so that they contact the agarose. Then, the slide cover 117 of the electrophoretic bath is pulled laterally to close. The reagent vial rack 118 (see FIG. 3) is provided with three holes numbered as 1, 2, and 3 from the front face of the machine and, in examination of a single item, a reagent is set in hole 2. To perform examination of two items, cholesterol and triglyceride, for example, a reagent for cholesterol is set in hole 1 and a triglyceride reagent in hole 3.

In the illustrated embodiment, 30 sample cups 119 of the sample table 114 (see FIG. 4B) are provided such that up to a maximum of 30 specimens may be electrophoresed at the same time. Two rows of 15 cups each are illustrated. It should be understood the number and arrangement of sample cups is only for illustrative purposes, is of a maximum of 30 specimens of two rows of 15 analytes for a single item. When examining samples as described above, for example, specimens from a first patient to fifth patient are placed in cups 1 and 11, 2 and 12, 3 and 13, 4 and 14, and 5 and 15. Specimens from a sixth patient to the tenth patient are placed in cups 16 and 26, 7 and 27, etc. The sample table 114 is provided with cleaning liquid and purified water for rinsing the same and for cleaning the applicator 112. Numeral 114-1 (FIG. 3) denotes filter paper for wiping out water from the applicator.

Figure 2B:
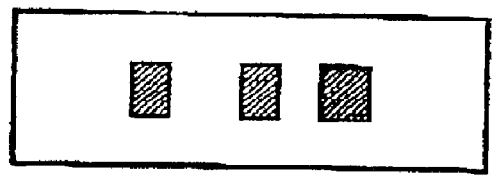

Upon completion of the above-described preparation for electrophoresis, a start instruction can be inputted from the keyboard 142 to the computer to thus provide a start instruction to the electrophoretic apparatus. As identified by the references numerals in FIG. 2, the electrophoretic apparatus applies the sample (S202) and starts electrophoresis (S204). When the electrophoresis is completed, reagent is deposited on the agarose film, (S206) including the electrophoresed or separated sample. A reaction is carried out for a predetermined time at a predetermined temperature (S208), fixed with a 5% acetic acid (S210) and the reaction mixture is dried (S212). As a result of such electrophoresis, an electrophoretic diagram as shown in FIG. 2B is obtained.

Figure 5:
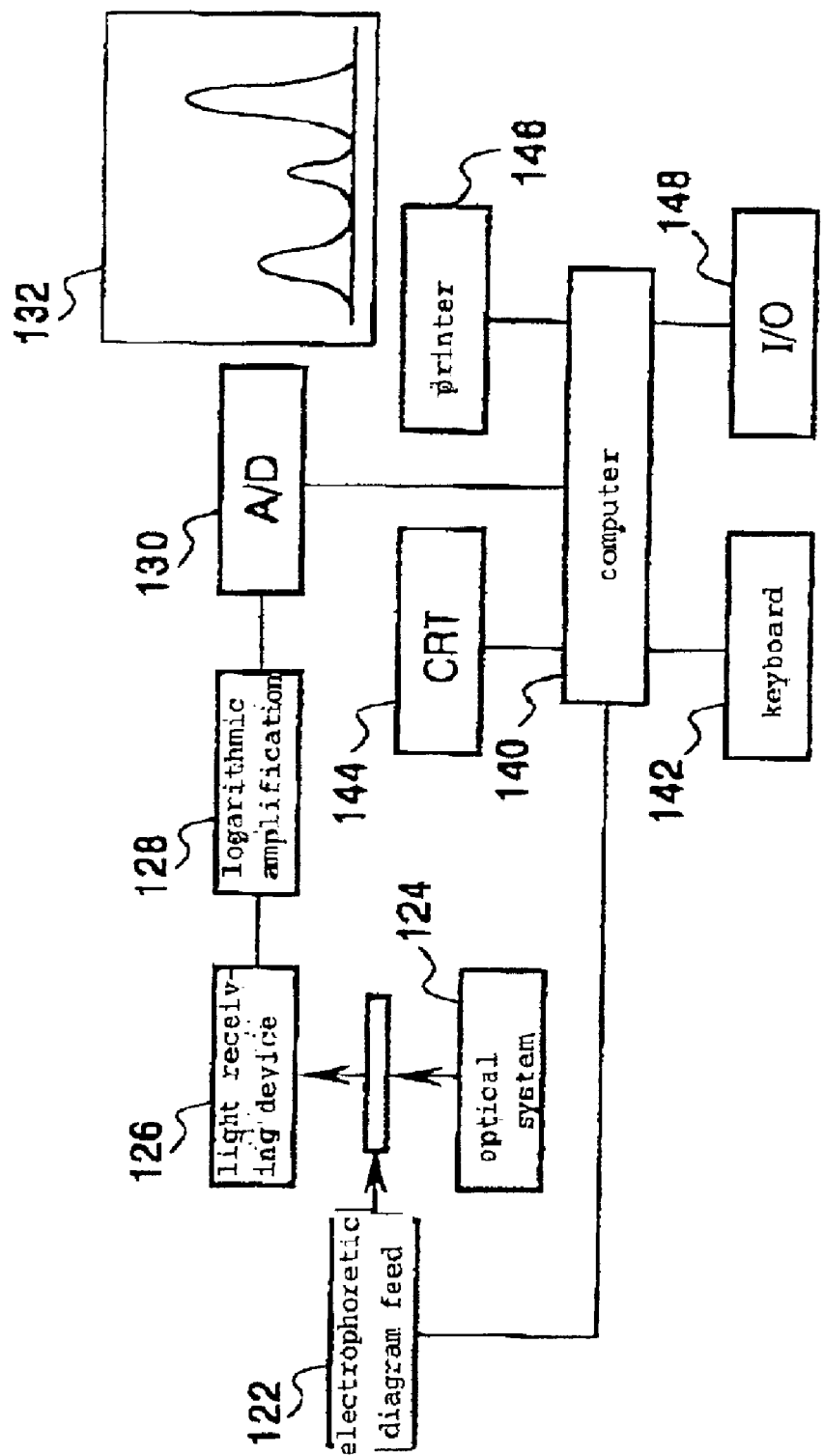
FIG. 5 is a block diagram illustrating the arrangement of a densitometer and a computer system.

The resulting electrophoretic diagram (e.g., of FIG. 2B) is analyzed using the densitometer 120 and the computer system. FIG. 5 shows operation of the densitometer and the like and a block diagram of the densitometer and the computer system, and operation of the densitometer and the like will be described with reference to FIG. 5.

Prior to the explanation of the operation, it must be emphasized that the invention will be explained in the context of two substances, cholesterol and triglyceride. Such explanation must be understood, however, to be merely illustrative and not limiting. The electrophoretic diagram shown in FIG. 2(b) is measured by placing it on an electrophoretic diagram feed 122 of the densitometer 120. Cholesterol and triglyceride have specific absorption wavelengths with the reagent. The reagent used in this examination is one which forms a formazane and absorbs light of 570 nm in wavelength, and the measurement is made at a wavelength of 570 nm. Measuring light emitted from an optical system 124 is passed through the electrophoretic diagram and strikes a light receiving device 126 to generate an electromotive force. When the measurement is started, the electrophoretic diagram feed 122 scans to pass the diagram in the measuring light, and the amount of light absorbed by a sample part provides a change in electromotive force. The amount of this change is received by the light receiving device 126 to achieve measurement. The amount of change received by the light receiving device 126 is logarithmically amplified by a logarithmic amplifier 128, converted by an A/D converter 130 into a digital value, and registered on a storage medium (e.g. hard disk) of the computer system. When an instruction is made to output the result, a graph 132 plotting the scanning direction on the axis of abscissas against integrated values on the axis of ordinates is displayed on the CRT 144 or outputted on the printer 146. Further, the computer 140 also converts each fraction into percentage from the integrated value of waveform, to determine concentration of each fraction from the previously determined total concentration. However, this measurement or result is difficult to understand because it is displayed for each item.

An a further example of the present invention, a case, where the present invention is realized as software for the computer system performing processing of the densitometer 120 as shown in FIG. 1 will be described below.

Figure 6:
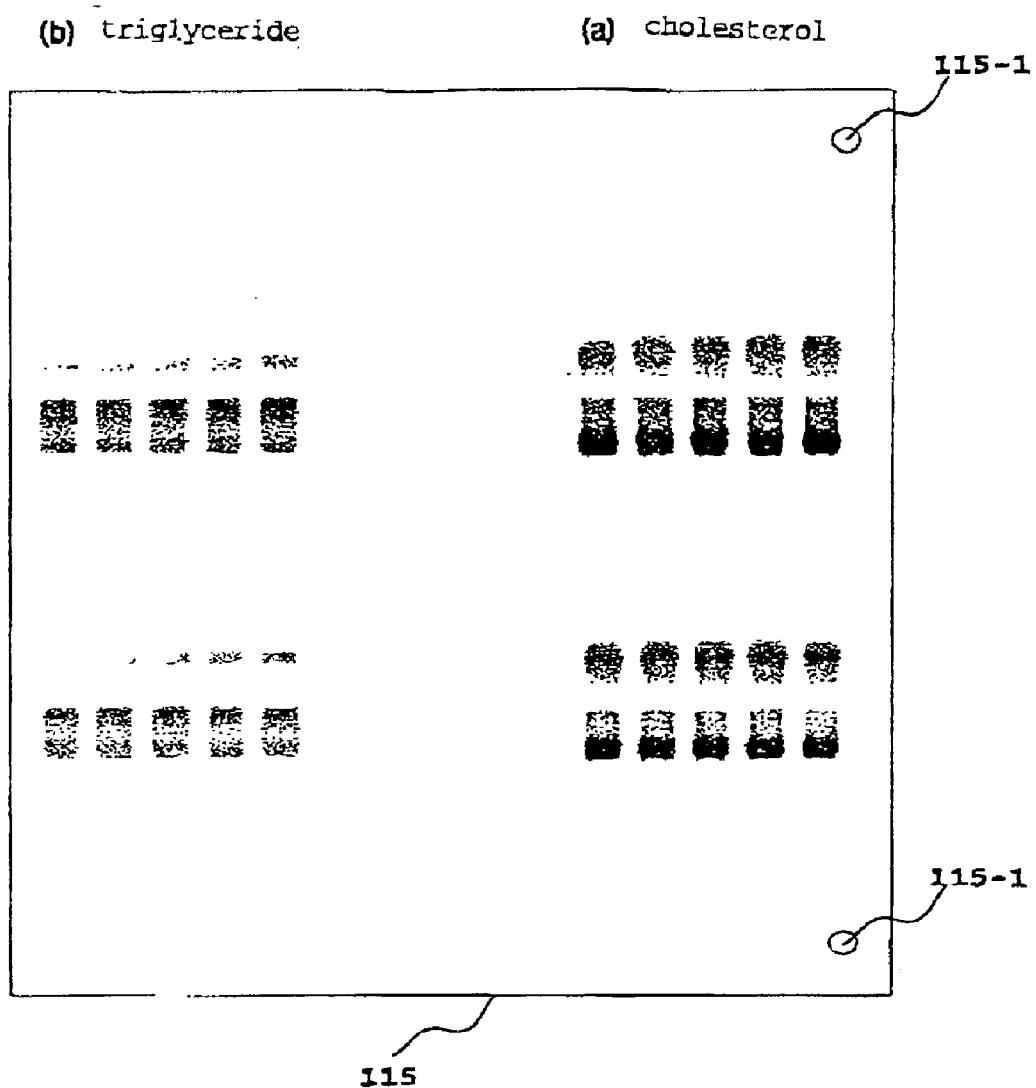
FIG. 6 is a diagram of multiple samples of lipid in serum obtained by an electrophoretic method and visualized.

FIG. 6 shows an electrophoretic diagram prepared using the electrophoretic apparatus 110. FIG. 6 is an electrophoretic diagram of cholesterol (diagrams A) and triglyceride (neutral fat)(diagrams B). Each diagram is scanned by the densitometer 120, and the resulting electrophoretic waveform is stored on a recording medium such as a hard disk. (Alternate internal and external storage media are contemplated by the present invention, and thus the reference to a hard disk should not be interpreted in a limiting sense.) The waveform resulting from the scanning is processed using software which is an embodiment of the present invention.

Figure 7:
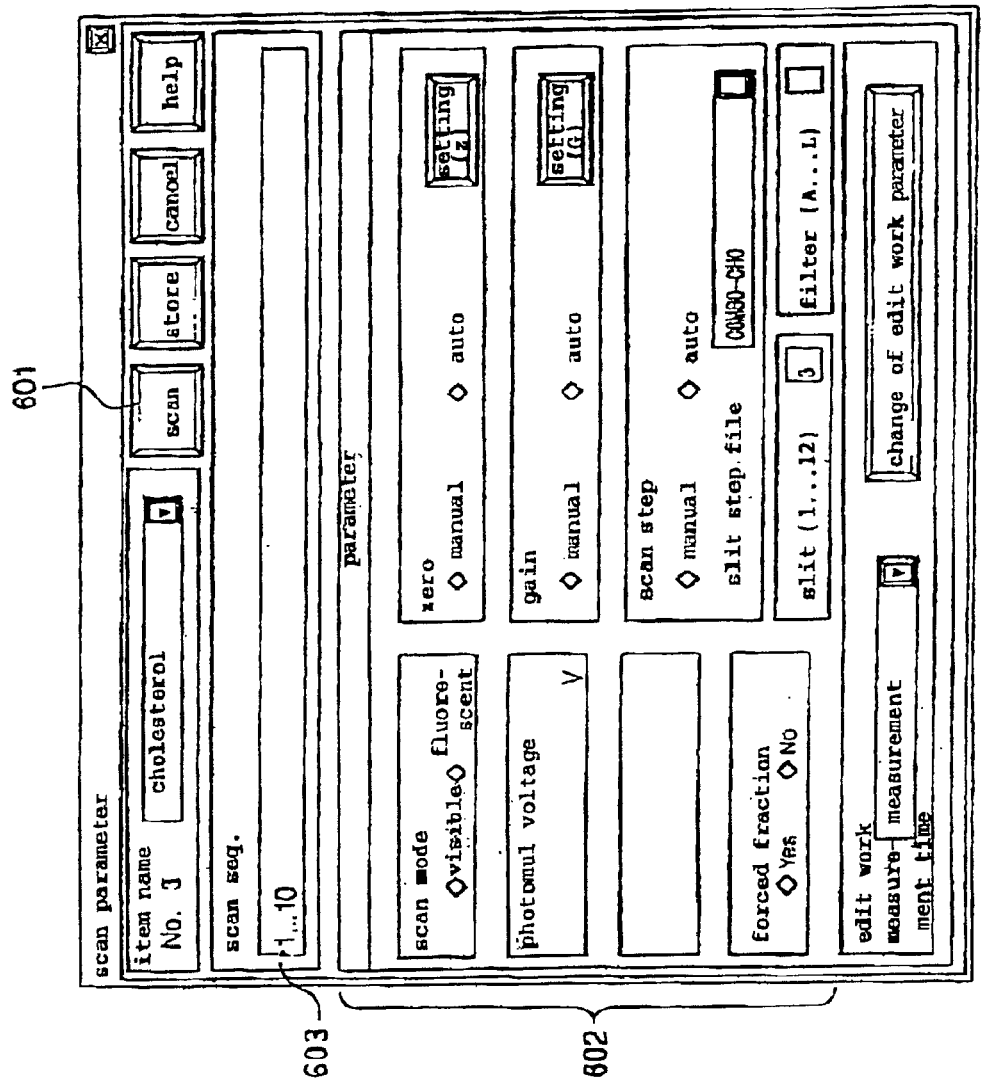
FIG. 7 is a diagram showing a display for setting a scanning condition.
Figure 9:
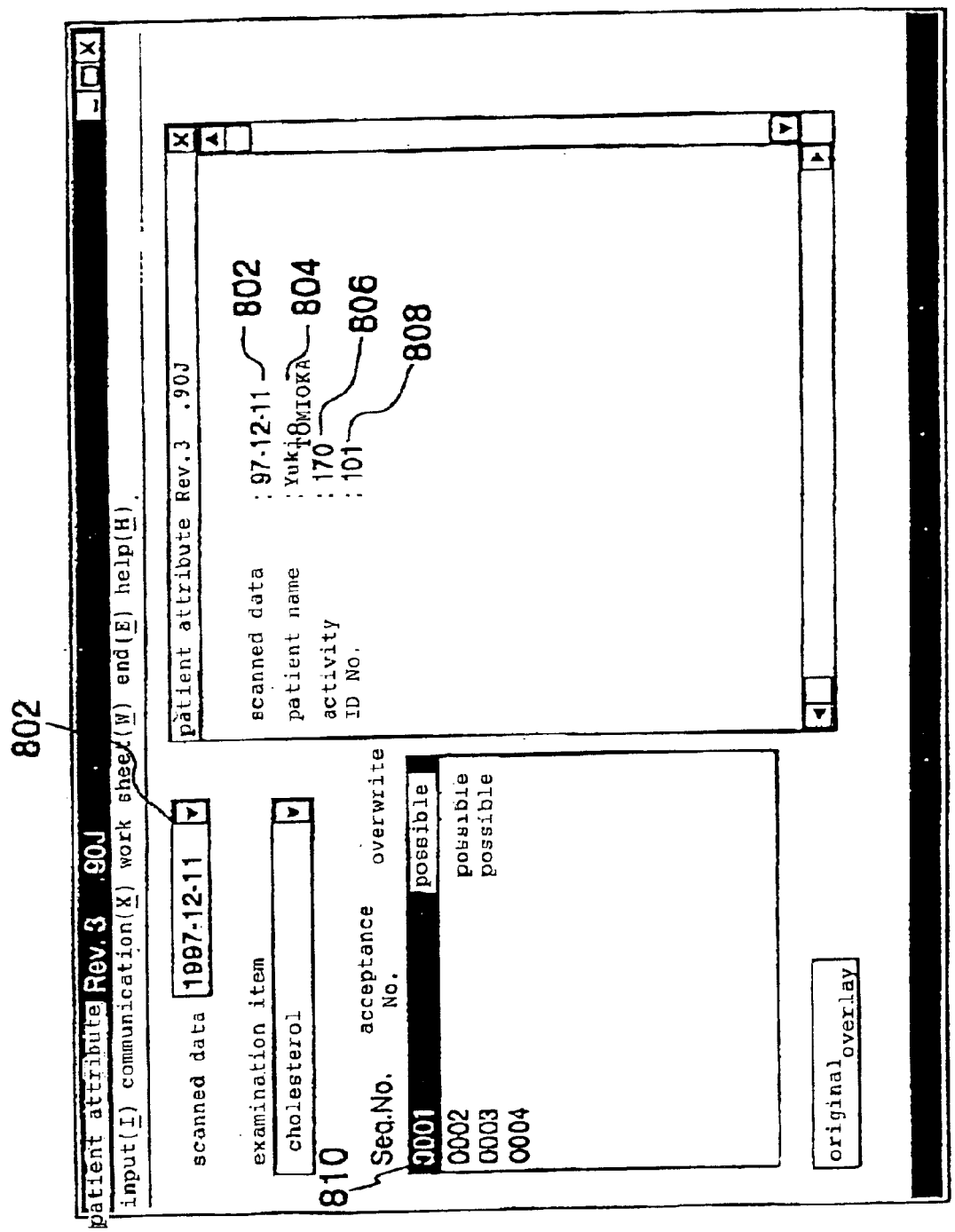
FIG. 9 is a diagram showing a display for setting an attribute.

FIGS. 7 to 9 show windows displayed on the CRT 144 of the computer system for inputting data on scanning condition and scanned subject (sample). In FIG. 7, a scanning parameter.(condition) is set by a parameter setting part 602 at the lower part. A preset default parameter can be used, and when it-is not required to be changed, it is sufficient to input only scan sequence 603, and a scan button 601 is clicked.

Further, a window for inputting attributes for the sample (analyte) is shown in FIG. 8 and FIG. 9. In FIG. 8 when cholesterol is selected as the examination item, the window of FIG. 9 is opened. Here, scanned date 802, sequence number. 810, patient identification number 808, and patient name 804 and the like and activity values (total concentration: absolute concentration) of cholesterol 806 which is in, separately measured are inputted. Still further, attributes are similarly inputted for triglyceride. Under this condition the diagram of FIG. 6 is scanned, and the obtained waveforms of two items of cholesterol and triglyceride are stored on a hard disk or the like.

Figure 10B:
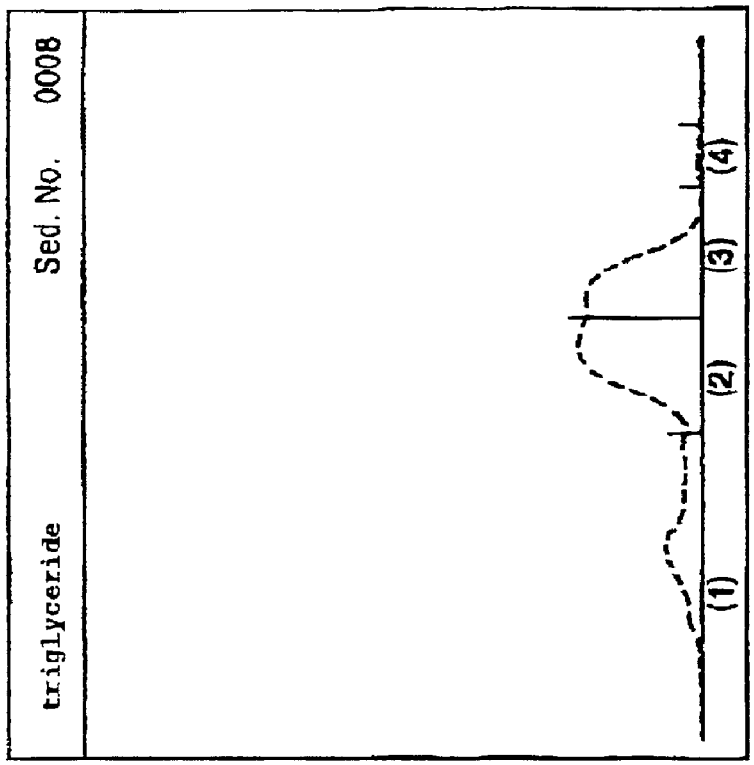
FIG. 10A and FIG. 10B, are a waveform diagrams obtained by a densitometer scanning an electrophoresed sample.
Figure 10A:
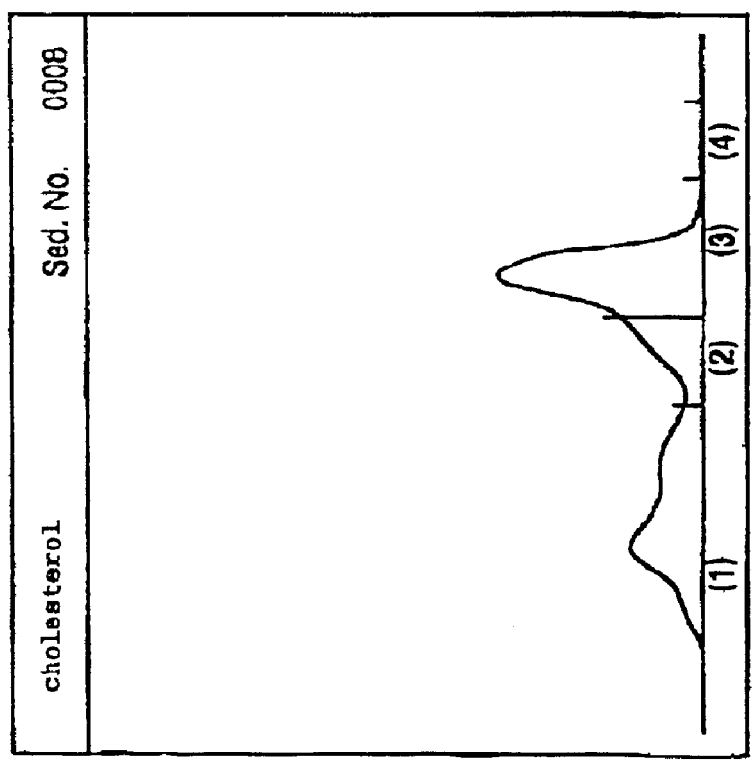
Figure 11:
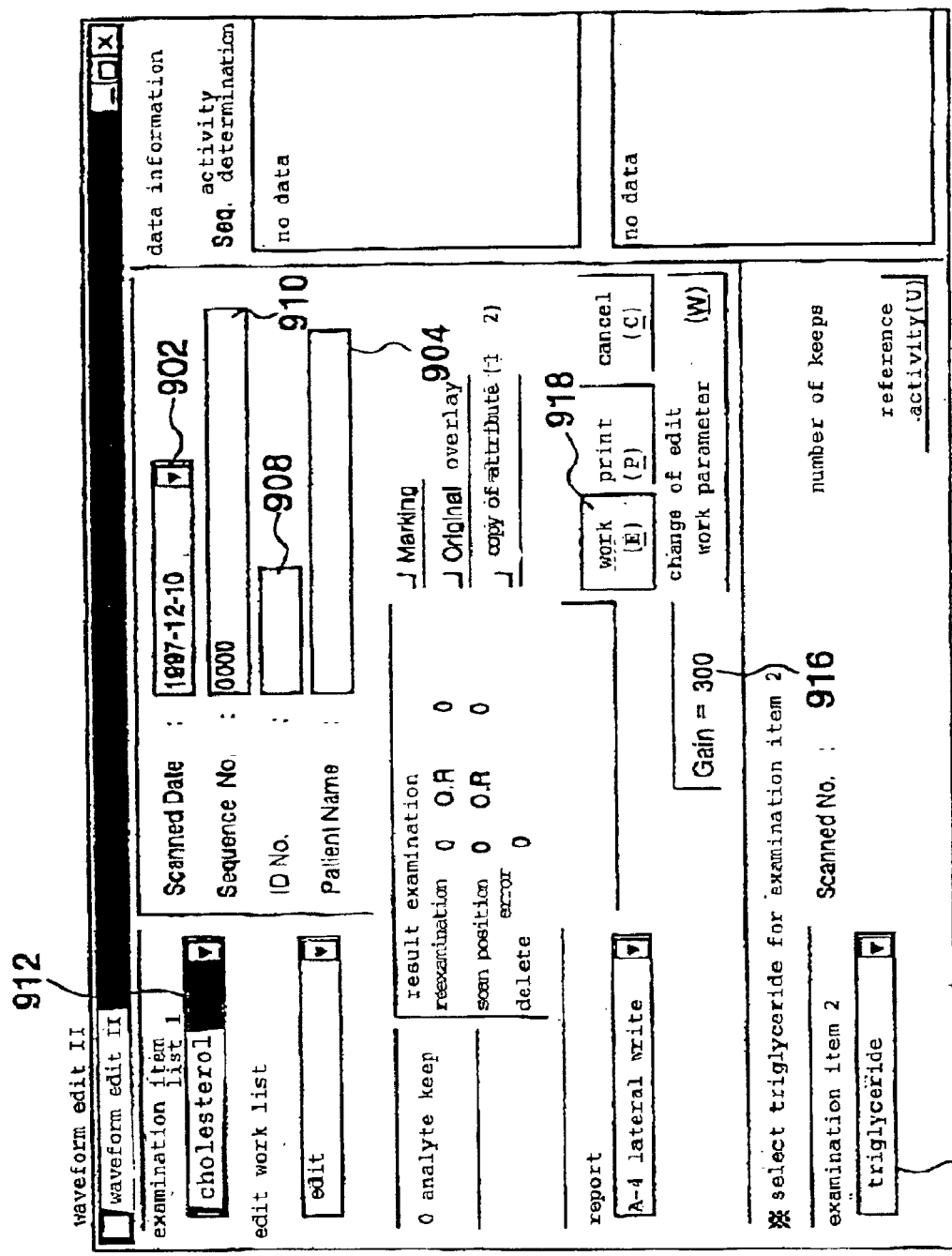
FIG. 11 is a diagram showing a display for designating display of two waveforms.

FIGS. 10A and 10B are examples of waveforms of two items of cholesterol and triglyceride which are thus stored on the hard disk by following the procedure which has just been described. In addition, to retrieve the scanning result for the two items of the same analyte stored on the hard disk onto the same window for observation, the window of waveform edit II is opened, which is shown in FIG. 11. Thus, the waveform corresponding to cholesterol and triglyceride of the same patient identification, patient name and the like can be designated.

Figure 12:
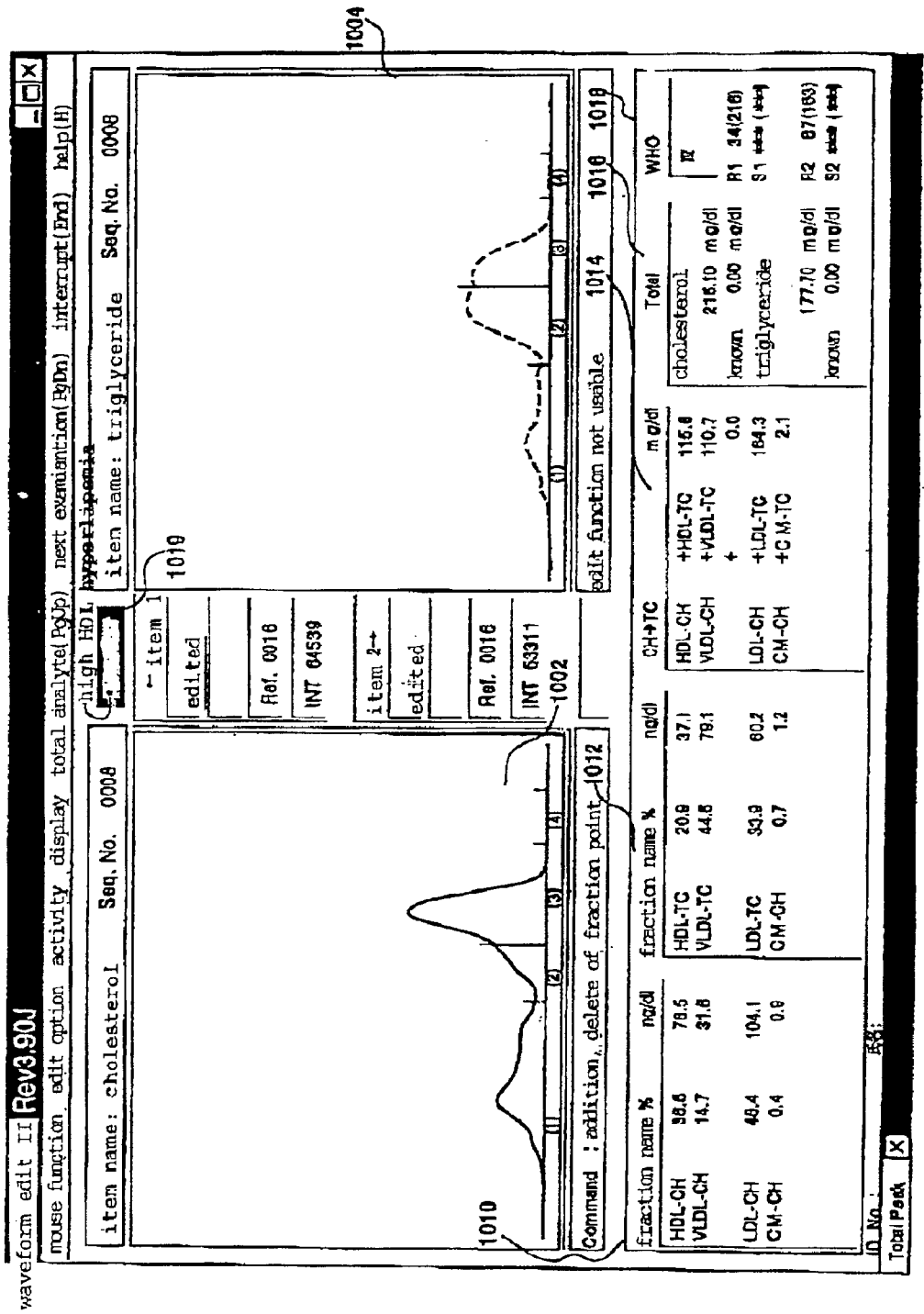
FIG. 12 is a diagram displaying two waveforms simultaneously at different places.
Figure 13:
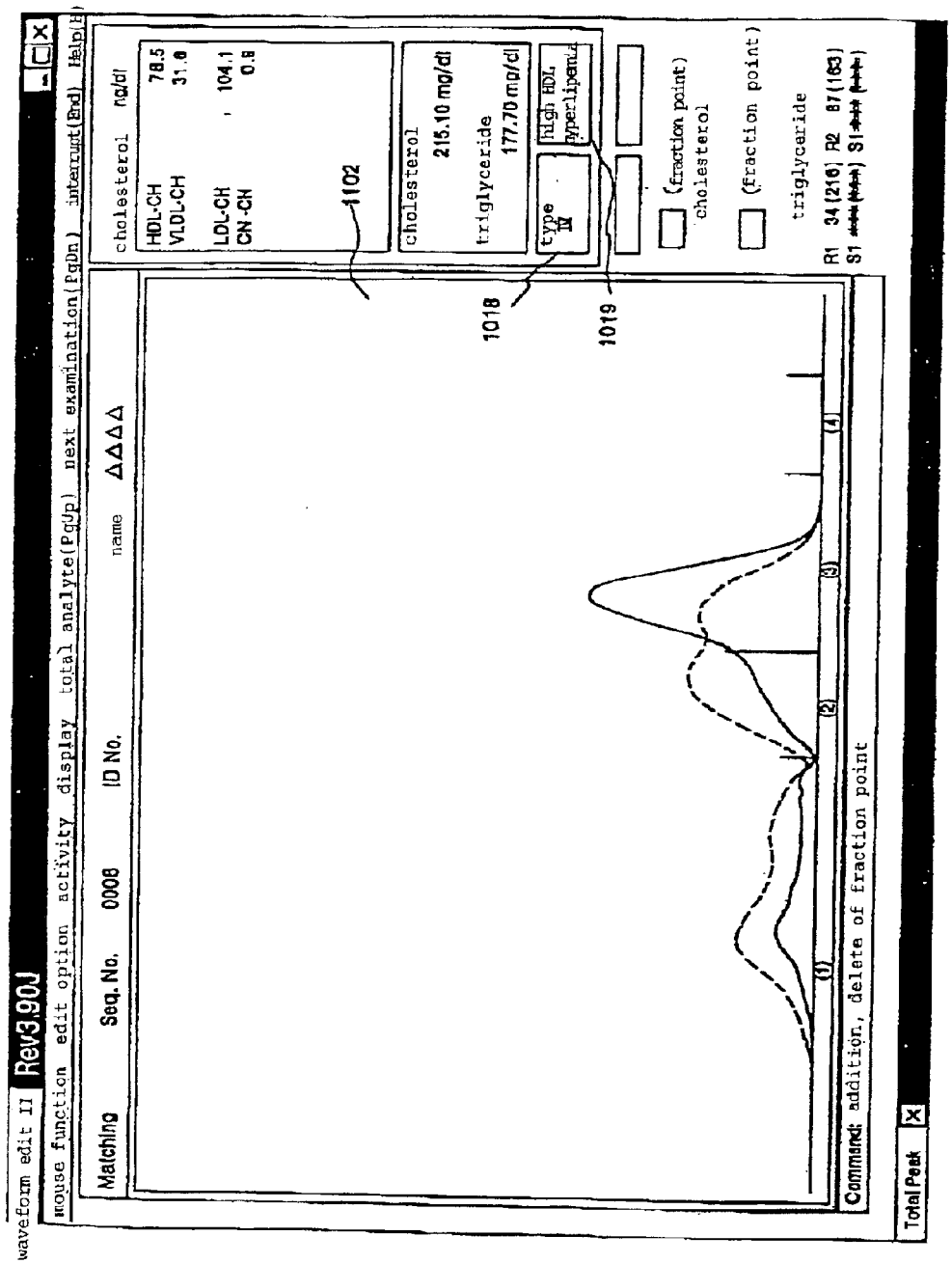
FIG. 13 is a diagram displaying two waveforms simultaneously and overlappedly.

To perform the above, items which can specify a scanned date (902)(FIG. 11), a sequence number, 910, an ID number 903, a patient name 904 and the like are inputted such as via the keyboard. For the purpose of explanation, cholesterol 912 is designated as an examination item 1, and triglyceride 914 as an examination item 2, i.e., the components of interest. The number 916 designated as gain is a coefficient to determine the size of displayed waveform. This is commonly used for the two waveforms. After completion of input of necessary items, when an operation button 918 can be clicked to display waveforms as shown in FIG. 12 and FIG. 13. In FIG. 12, discrete waveform diagrams as shown in FIG. 10A and FIG. 10B are displayed as a cholesterol waveform diagram 1002 and a triglyceride waveform diagram 1004 side by side on the same window. FIG. 13 displays a waveform diagram 1102 wherein waveforms of cholesterol and triglyceride are overlapped or superimposed.

In order to compare two waveform diagrams or display them overlappedly, (superimposed) the waveform diagrams should never be changed with scanning conditions and the like as seen in the prior art.

Therefore, in the present invention, it is solved by correlating one unit of absolute concentration with one unit of size of waveform. For example, a total integrated value of analog data determined by measurement is divided by absolute concentration to determine an integrated value per one unit of absolute concentration, and the waveform is displayed using the integrated value as one unit of waveform to obtain a waveform corresponding to the concentration. That is, area of waveform (integrated value) and absolute concentration (total concentration) are set to have a constant proportional relation. The thus corrected waveform is recorded on a recording medium such as a hard disk. Alternatively, the integrated value of analog data determined by measurement may be recorded, as is, on the recording medium which is processed each time as necessary. When the recorded data is read and displayed as a graph, the waveforms can be compared with each other.

Waveforms which are normalized so that the waveform area (integrated value) and absolute concentration (total concentration) are in a constant proportional relation are shown in FIG. 12 and FIG. 13. FIG. 12 and FIG. 13 may be adapted to be selected by pressing a specific button on the keyboard.

In FIG. 12, the number of fractions (1) to (4) and analytical results determined from the total concentration are displayed on the lower part of waveform diagrams 1002 and 1004. HDL (high-density lipoprotein), VLDL (very low density lipoprotein), LDL (low-density lipoprotein), CM (chylomicron) in cholesterol are displayed in 1010. The same analytical results for triglyceride are displayed in 1012. A summation of both cholesterol and triglyceride is displayed in 1014. WHO phenotype classification and high HDL hyperlipemia are displayed in 1018 and 1019. The WHO classification, as described above, classifies as to which of lipoprotein is increased.

Figure 14:
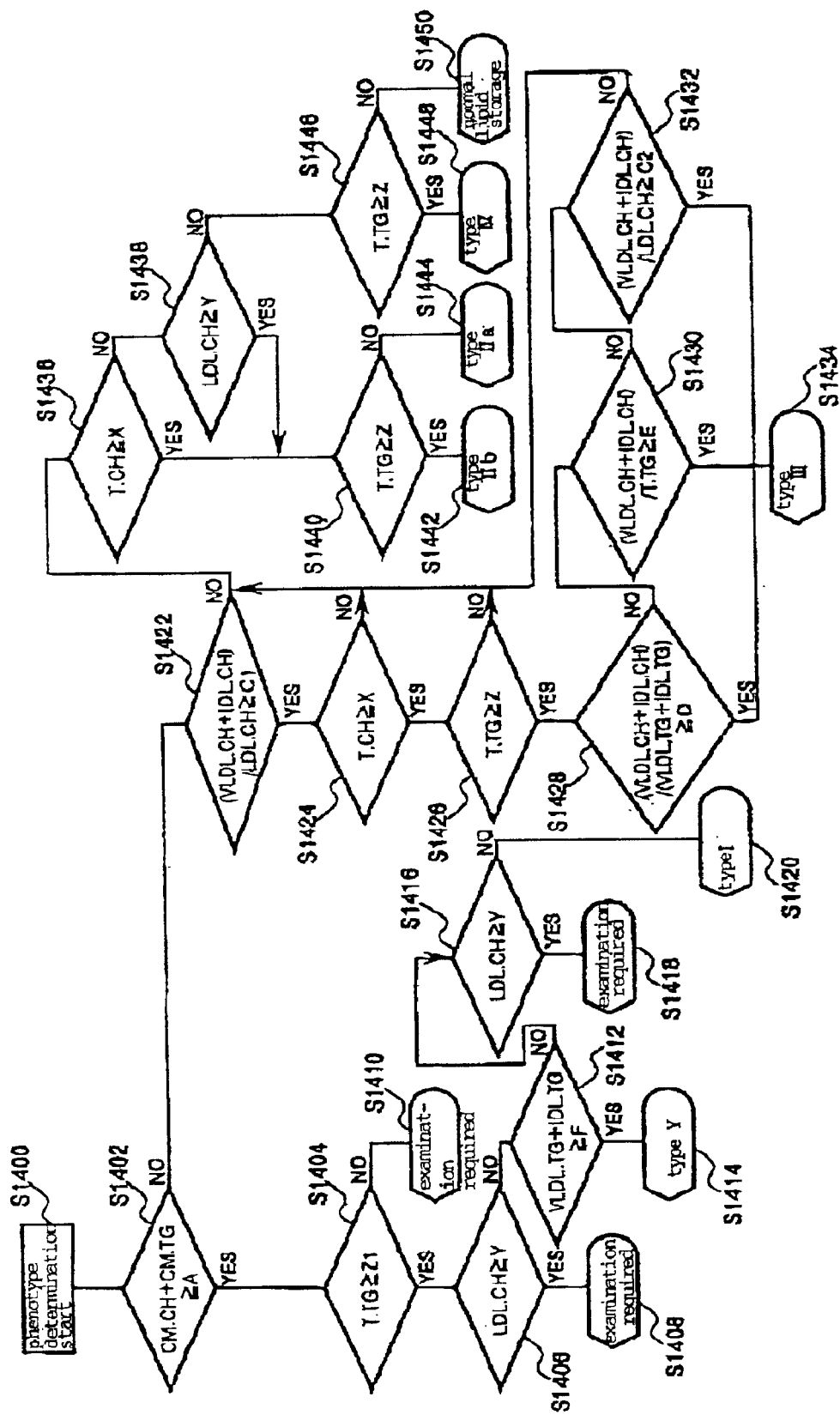
FIG. 14 is a flow chart showing processing of WHO phenotype judgment.

Determination of the WHO classification will be described using the flow chart of FIG. 14. In FIG. 14, A is phenotype determination start; B is examination required; C is type V; D is normal lipid storage. Here, symbols used in the flow chart are as follows. "T CH": total cholesterol; "HDL.CH": HDL cholesterol; "VLDL.CH": VLDL cholesterol; "IDL.CH": IDL cholesterol; "LDL.CH": LDL cholesterol; "CM.CH": chylomicron, cholesterol; "T.TG": total triglyceride; "HDL.TG": HDL triglyceride; "VLDL.TG": VLDL triglyceride; "IDL.TG": IDL triglyceride; "LDL.TG": LDL triglyceride; "CM.TG": chylomicron, triglyceride. Furthermore, as examples of reference values which may be imput into the computer and thus used for automatic decision, i.e., computerized judgments:

| | |
|---|---|
| Total cholesterol (X): | 220 mg/dl |
| LDL cholesterol (Y): | 150 mg/dl |
| HDL cholesterol (B): | 70 mg/dl |
| (VLDL.CH + IDL.CH)/T.TG (E): | 0.25 |
| VLDL.TG + IDL.TG (F): | 150 mg/dl |
| Total triglyceride (Z): | 150 mg/dl |
| Total triglyceride (Z1): | 400 mg/dl |
| CM.CH + CM.TG (A): | 100 mg/dl |
| (VLDL.CH + IDL.CH\V (VLDL.TG + IDL.TG) (D): | 0.42 |
| (VLDL.CH + IDL.CH)/LDL.CH (C1): | 0.8 |
| (VLDL.CH + IDL.CH\ULDL.CH (C2): | 1.3 |

Specifically, in the flow chart of FIG. 14, phenotype determination is started from examination of the sum of chylomicron cholesterol (CM.CH) and chylomicron triglyceride (CM.TG) (S1402). When the sum is greater than reference value A (YES in S1402), a determination is made as to whether or not total triglyceride (T.TG) obtained by another examination is greater than reference value Z1 (S1404). When total triglyceride (T.TG) is not greater than Z1 (NO in S1404), another examination is-required. When the value is greater (YES in S1404), low-density lipoprotein cholesterol (LDL.CH) is examined (S1406). When low-density lipoprotein cholesterol (LDL.CH) is greater than reference value Y (YES in S1406), another examination is required (S1408). When the value is smaller (NO in S1406), a further examination is made as to whether or not the sum of very low density lipoprotein triglyceride and intermediate density lipoprotein triglyceride (VLDL.TG+DL.TG) is greater than reference value F (S1412). When the sum (VLDL. TG+IDL. TG) of very low density lipoprotein triglyceride and intermediate density lipoprotein triglyceride (VLDL.TG+IDL.TG) is greater than reference value F (YES in S1412), phenotype is determined to be "type V" (S1414).

When the value is smaller (NO in S1412), an examination is made as to whether or not low-density lipoprotein cholesterol greater than reference value Y (LDL.CH) is (S1416). When low-density lipoprotein cholesterol (LDL. CH) is greater than reference value Y (YES in S1416), another examination is required (S1418). When it is smaller (NO in S1416), lipid phenotype of the examination subject is "type I" (S1420).

When the sum of chylomicron cholesterol (CM) and chylomicron triglyceride (CM.TG) is examined (S1402), if it is smaller than reference value A-(NO in S1402), a ratio of the sum of very low density lipoprotein cholesterol and intermediate density lipoprotein cholesterol (VLDL.CH+ IDL.CH) and low-density lipoprotein cholesterol (LDL.CH) is determined, which is compared with reference value C1 (S1422). When the ratio is greater than reference value C1 (YES in S1422), total cholesterol (TCH) is compared with reference value X (S1424). When greater (YES in S1424), total triglyceride (T.TG) is compared with reference value Z (S1426). When it is greater than reference Z, a ratio of the sum of very low density and intermediate density lipoprotein cholesterol (VLDL CH+IDL.CH) to the sum of very low density and intermediate density lipoprotein triglyceride (VLDL.TG+IDL.TG) is compared with reference value D (S1428). When the ratio is greater than reference value D (YES in S1428), it is determined to be phenotype III (S1434). Similarly, when the result is NO in S1428, a ratio of the sum of very low density lipoprotein cholesterol and intermediate lipoprotein cholesterol (VLDL.CH+IDL.CH) to total triglyceride (T. TG) is compared with reference value E (S1430). When it is greater than reference value E (YES in S1430), it is determined to be "phenotype III". When the result is No in S1430, a ratio of the sum of very low density lipoprotein cholesterol and intermediate density lipoprotein cholesterol (VLDL.CH+IDL.CH) to low-density lipoprotein cholesterol (LDL.CH) is compared with reference value C2 (S1432). When it is greater than reference value C2 (YES in S1432), it is further determnined to be phenotype of "type III".

When phenotype "III" is not determined in step S1422 to step S1432, all cases are examined as to whether or not total cholesterol (T.CH) is greater than reference value X (S1436). When total cholesterol (T.CH) is smaller than reference value X (NO in S1436), a further examination is made as to whether or not low-density lipoprotein cholesterol (LDL.CH) is greater than reference value Y (S1438). When it is greater than reference value Y (YES in S1438), an examination is made as to whether or not total triglyceride (T.TG) is greater than reference value Z (S1440). When it is greater (YES in S1440), it is determined to be "type IIb", and when it is smaller (NO in S1440), it is determined to be "type Iia".

When the result is NO in the above step S1438, an examination is made as to whether or not total triglyceride (T.TG) is greater than reference value Z (S1446), when greater (YES in S1446) it is "type IV", and when smaller (NO in S1446) it is normal lipid storage (normal).

Figure 15:
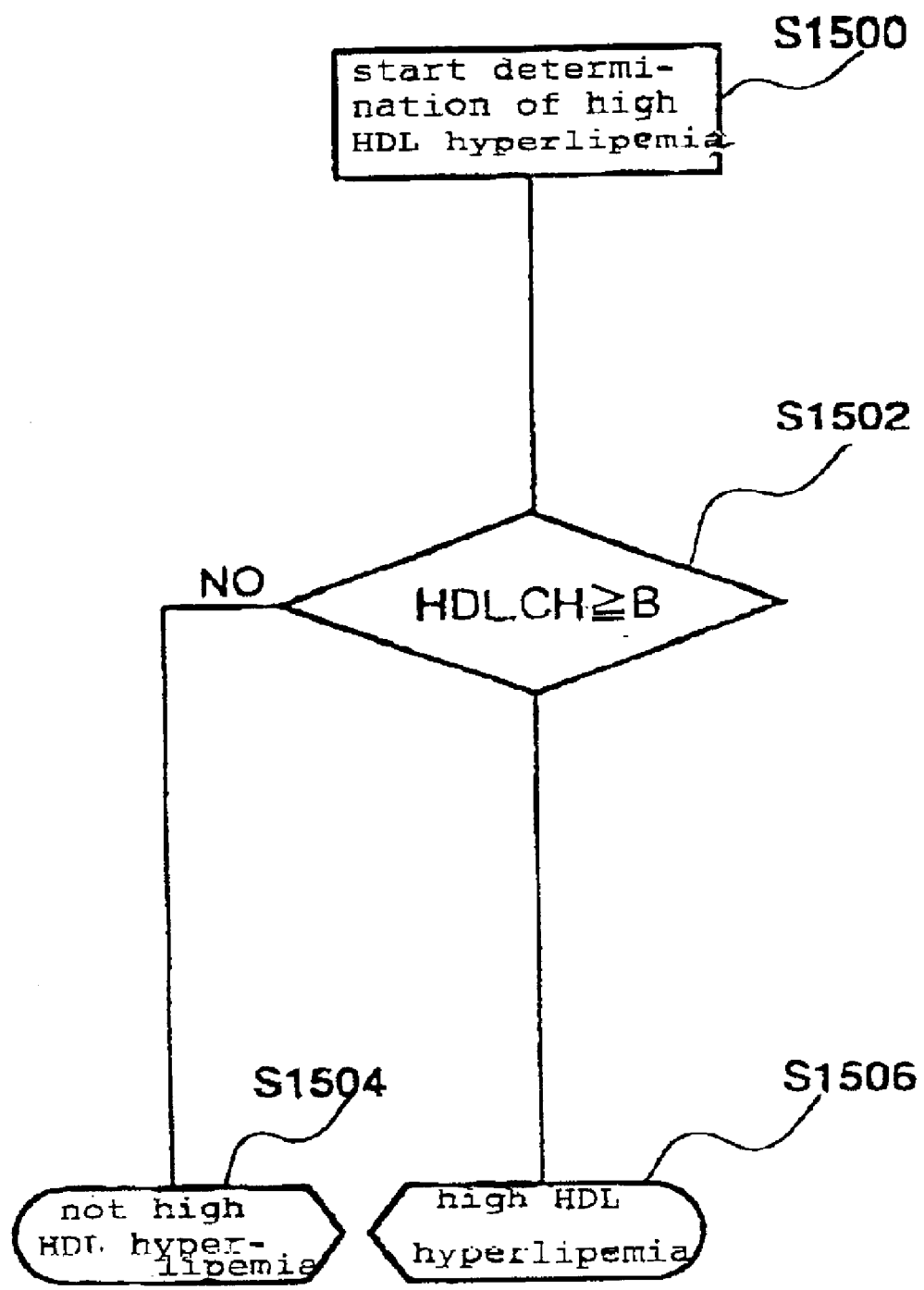
FIG. 15 is a flow chart showing judgment processing of high HDL hyperlipemia.

Further, FIG. 15 shows the decision making procedure for displaying high HDL hyperlipemia. When high-density lipoprotein cholesterol (HDL.CH) is greater than reference value B (YES in S1502), it is judged to be high HDL hyperlipemia (S1506).

When classification is made automatically using analytical results of cholesterol and triglyceride as described above, it is easy to establish plans for diagnosis and dietary treatment and pharmaceutical treatment according to the diagnosis.

Figure 16A:
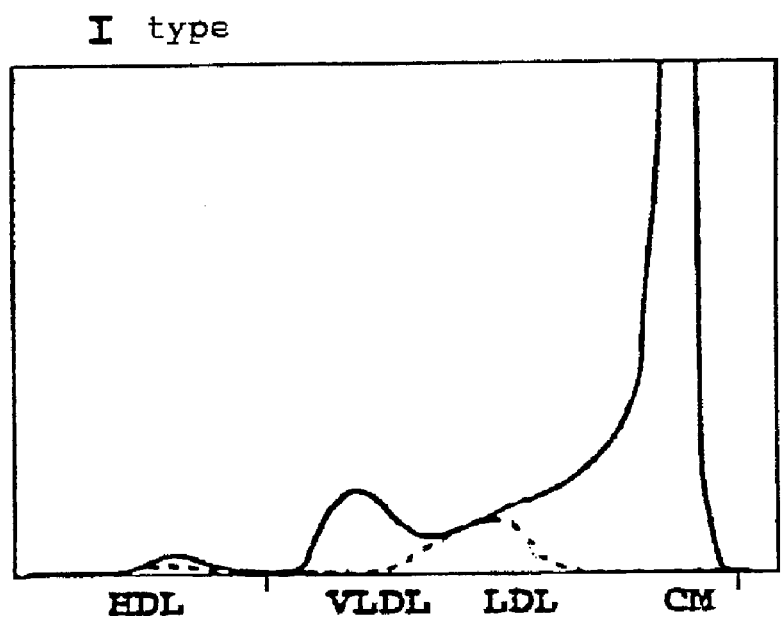
FIG. 16A and FIG. 16B, are diagrams showing the relationship between waveforms of cholesterol and triglyceride and WHO phenotype (types I and IIa)
Figure 16B:
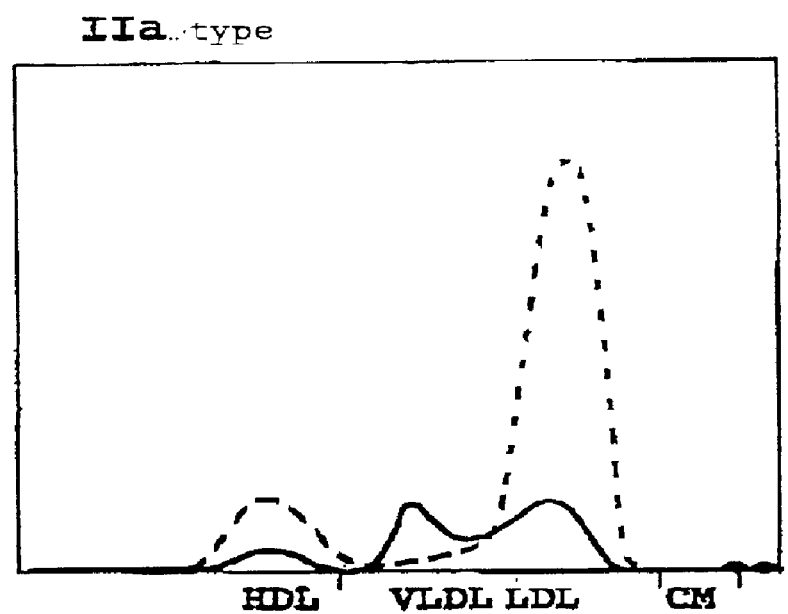
Figure 17A:
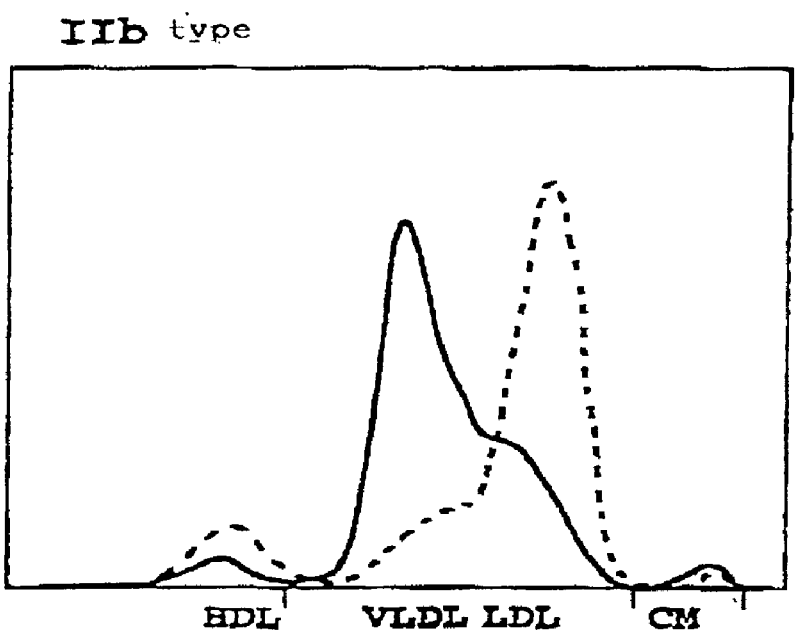
FIG. 17A and FIG. 17B, are diagrams showing the relationship between waveforms of cholesterol and triglyceride and WHO phenotype (types IIb and III)
Figure 17B:
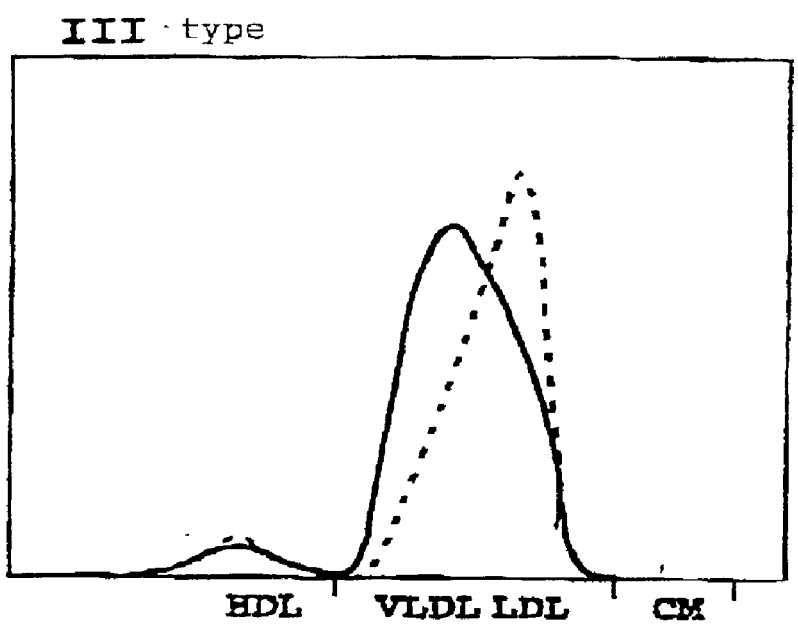
Figure 18A:
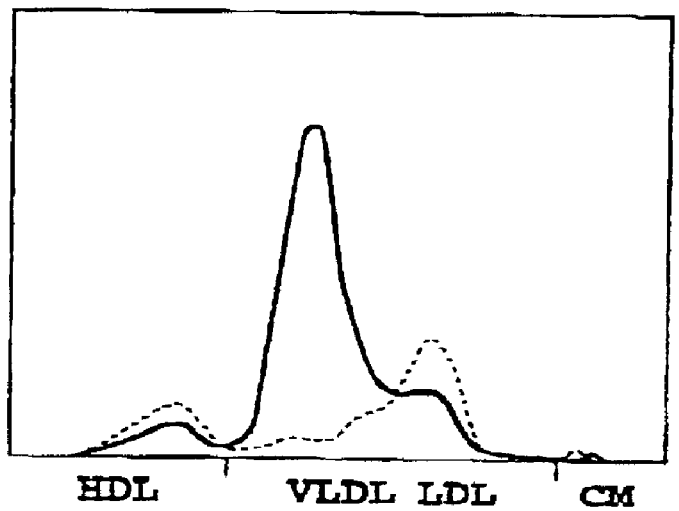
FIG. 18A and FIG. 18B, are diagrams showing the relationship between waveforms of cholesterol and triglyceride and WHO phenotype (types IV and V)
Figure 18B:
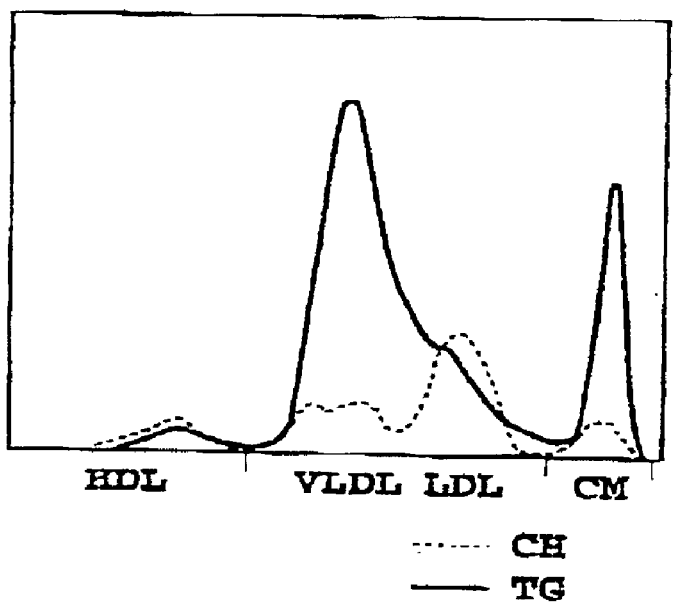

Still further, by normalizing and overlapping the waveforms of cholesterol and triglyceride as shown in FIG. 13, respective patterns of WHO classification can be clearly shown, and this is shown in FIG. 16 to FIG. 18. As shown in FIG. 16 to FIG. 18, by normalizing and overlapping electrophoretic diagrams of cholesterol and triglyceride, phenotype determination can be easily performed.

Figure 19:
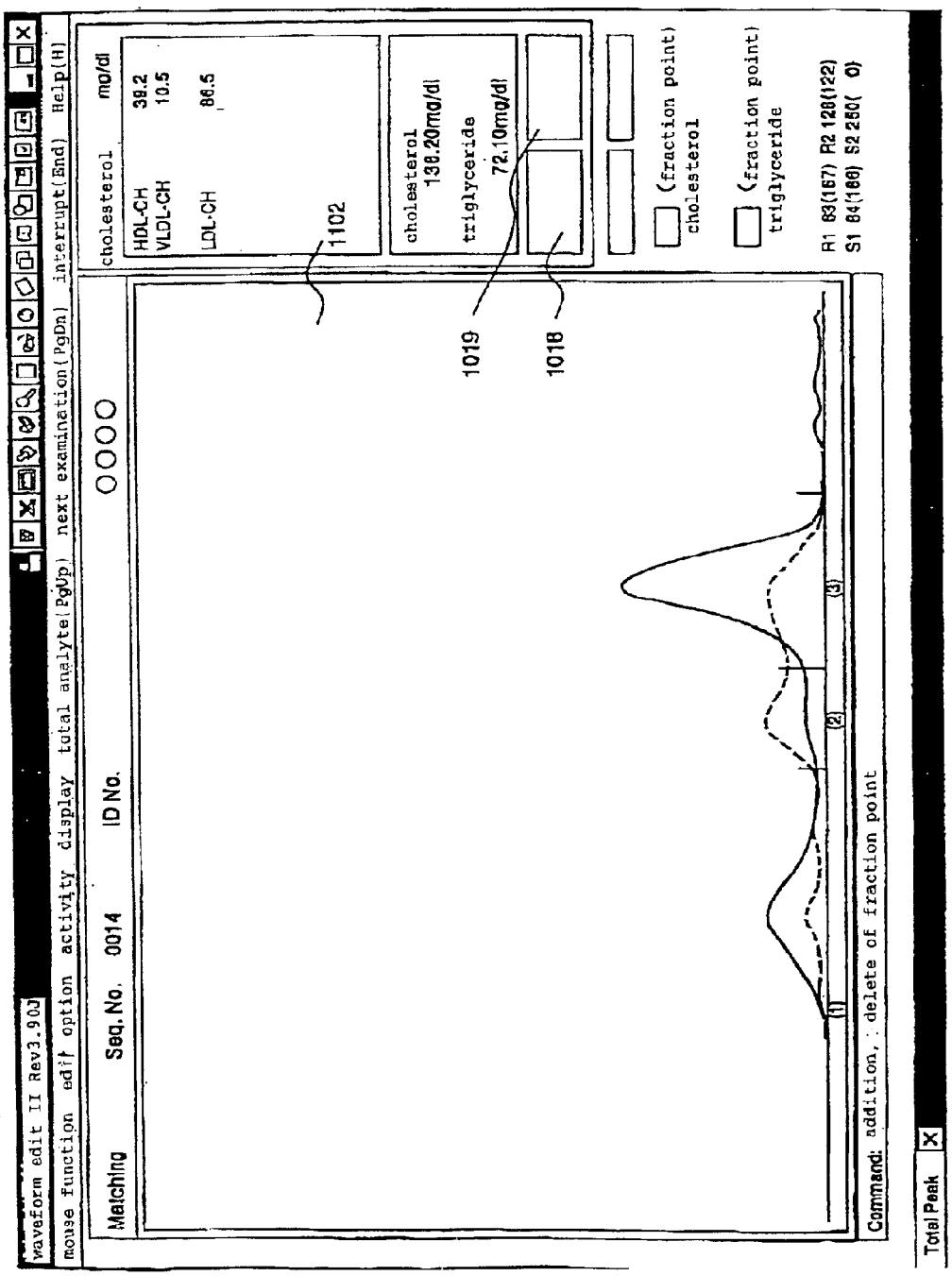
FIG. 19 is a waveform showing a normal lipid.

Yet further, FIG. 19 is a waveform diagram of a normal patient. As can be seen from FIG. 16 to FIG. 19, when two waveforms are overlapped, features of respective phenotypes are clearly shown, thereby providing definite judgment.

Figure 20:
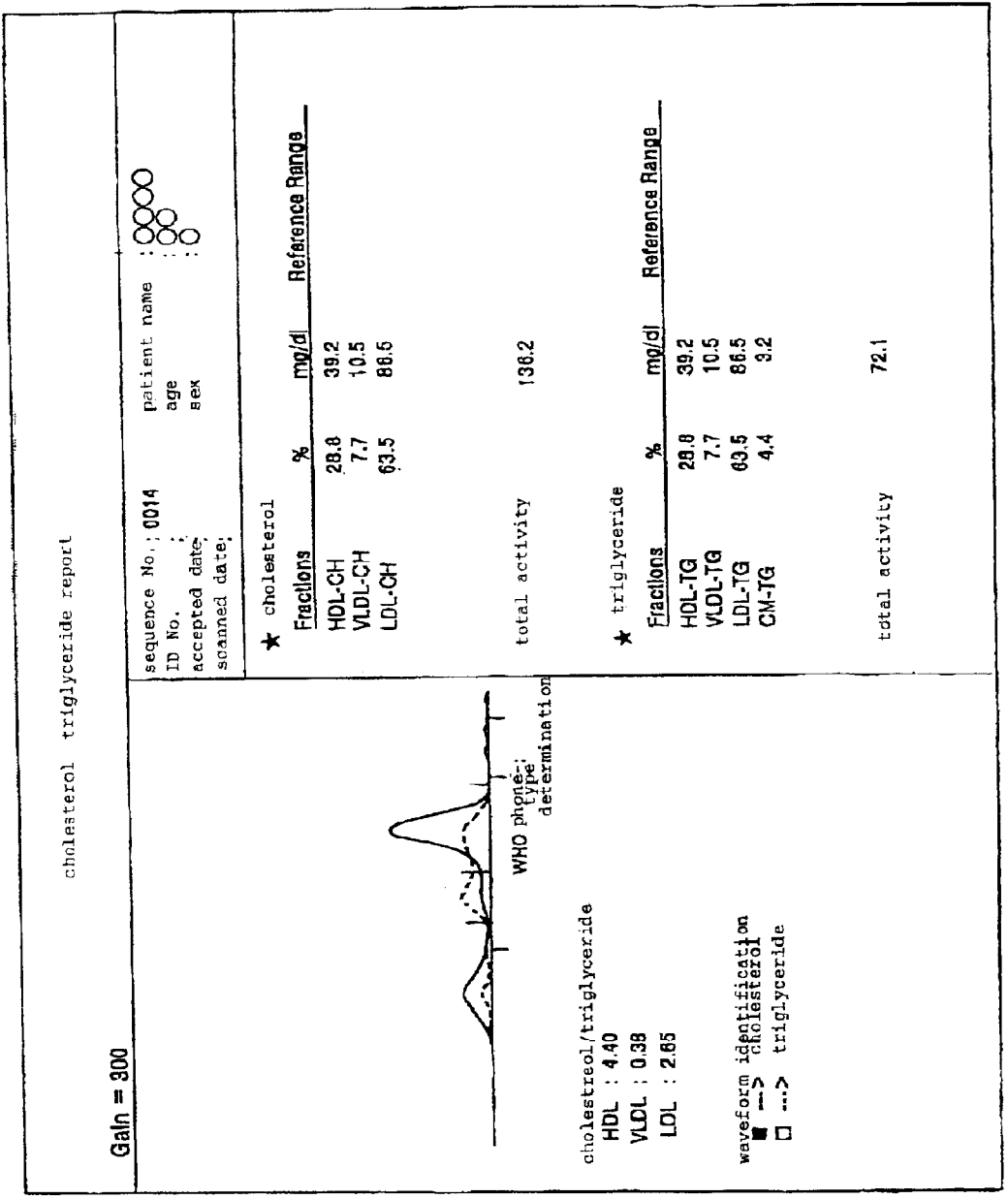
FIG. 20 is a diagram showing a printed-out chart of FIG. 19.

The waveform diagram displayed on the above window can be outputted from the printer 146 in FIG. 1 by an instruction. For example, a printed out result of waveform diagram of FIG. 19 is shown in FIG. 20.

In the above description, examination of lipid in blood is described using two items of cholesterol and triglyceride. However, the present invention is not limited to these two examinations. For example, the present invention can be applied to those which can be classified by combinations of two or more different examinations such as examination of phospholipid and examination of cholesterol, and the like. As described above, since it has been impossible in the prior art to display size of waveform and concentration in a constant proportional relation, waveform diagram is not utilized except for ratio change condition and concentration. Since, in the present invention, waveform and concentration can be displayed in a constant proportional relation, two measurements can be overlapped for comparison, thereby enabling more exact understanding of lipid metabolic condition.

An advantage of the present invention is that the examination result is not affected by deviation of analyte amount and difference in color development amount between samples. Therefore, using waveform, diagrams by the densitometer, waveform, diagrams detected in time series of the same analyte or waveform diagrams of different analytes can be similarly compared.

When observing data in time series of waveform diagrams according to the present invention, fine changes can be found as changes in amount which are useful for observation with the passage of time. In addition, since changing conditions can be understood, the measurements are useful for studies of metabolism. Further, changes in conditions of a patient can be easily explained with changes in waveform.

When the outputted waveform is too high or low in height, the coefficient set as gain 916 is changed. As a result, an output waveform of an appropriate size proportional to the concentration unit can be obtained.

In the above description, input for setting the total concentration or the like is described to be made from the keyboard 142, however, it may be externally inputted through an 1/0 interface 148 of FIG. 5 or the like. In FIG. 5, value of the densitometer is analog/digital converted after the logarithmic amplifier 128 and inputted in the computer 140. However, alternatively, it is possible that an analog signal from the light receiving device is converted to a digital signal, which is inputted to the computer, and logarithmic calculation is carried out by the computer.

Further, in the above description, examples are described for samples by electrophoresis of serum lipid, however, the present invention can be used for samples separated by capillary electrophoresis and those separated by electrophoresis on substrate films of cellulose acetate, agoras, agar, polyacrylamide gel, starch and the like and samples developed to thin layer chromatography.

Not only samples of electrophoresis, the present invention can also be used for those by a liquid chromatographic apparatus and a gas chromatographic apparatus.

As described above, since the present invention is possible to automatically perform judgment of phenotype of hyperlipemia and high HDL hyperlipemia from examination results of cholesterol and triglyceride, personal difference of judgment can be eliminated. In addition, using the judgment result of phenotype or the like, establishment of treatment plan is simplified.

Further, since waveform diagrams of cholesterol and triglyceride can be overlappedly observed, feature of phenotype is easily understood. Still further, when the examination results are observed in time series, changes of respective fractions, that is, an increase or decrease of fraction component is understood, which is useful for observation of treatment effect, especially of pharmacological effect, and explanation to the patient is thus simplified.

The foregoing is a complete description of the invention. Examples have been presented in a non-limiting, illustrative fashion. The invention, therefore, should be limited only by the following claims.

What is claimed is:

1. An examination data processing apparatus for analyzing a blood specimen containing a plurality of lipoproteins and computationally determining a lipid phenotype, the apparatus comprising:

means for integrating a plurality of optical density waveforms to calculate an integrated value for each optical density waveform, the optical density waveforms being formed by conducting electrophoresis on the blood specimen to obtain an electrophoretogram for each of a plurality of different lipoprotein components and optically scanning the electrophoretograms to obtain the optical density waveforms;

means for normalizing each optical density waveform using a corresponding integrated value to produce a plurality of normalized optical density waveforms;

means for storing the plurality of normalized optical density waveforms;

means for calculating totals of the different lipoprotein components for at least some of the plurality of lipoproteins using the normalized optical density waveforms;

means for comparing the totals to corresponding reference values; and means for determining a lipid phenotype based on the comparison of the totals to the corresponding reference values.

2. The apparatus of claim 1, wherein the lipoprotein components are triglyceride and cholesterol.

3. A recording medium storing a program to carry out a function of the examination data processing apparatus according to claim 2.

4. The apparatus of claim 1, wherein the plurality of lipoproteins include high density lipoprotein, low density lipoprotein, very low density lipoprotein, and chylomicron.

5. A recording medium storing a program to carry out a function of the examination data processing apparatus according to claim 1.

6. A device for analyzing a blood specimen containing a plurality of lipoproteins and computationally determining a lipid phenotype, the apparatus comprising:

a storage medium for storing a plurality of optical density waveforms for different lipoprotein components of the blood specimen, the optical density waveforms being formed by optically scanning a plurality of corresponding electrophoretograms, the electrophoretograms being formed by conducting electrophoresis on the blood specimen; and a computer connected to the storage medium, the computer being configured to perform the steps of integrating each of the optical density waveforms to produce an integrated value for each optical density waveform;

normalizing each optical density waveform using a corresponding integrated value to produce a plurality of normalized optical density waveforms;

calculating totals of the different lipoprotein components for at least some of the plurality of lipoproteins using the normalized optical density waveforms;

comparing the totals to corresponding reference values; and determining a lipid phenotype based on the comparison of the totals to the corresponding reference values.

7. The device of claim 6, wherein the lipoprotein components are triglyceride and cholesterol.

8. The device of claim 6, wherein the plurality of lipoproteins include high density lipoprotein, low density lipoprotein, very low density lipoprotein, and chylomicron.

9. A method for analyzing a blood specimen containing a plurality of lipoproteins and computationally determining a lipid phenotype comprising the steps of:

producing an electrophoretogram for each of a plurality of different lipoprotein components of the blood specimen;

optically scanning each electrophoretogram to produce a plurality of optical density waveforms;

integrating each of the optical density waveforms to produce a corresponding integrated value for each optical density waveform;

normalizing each optical density waveform using the corresponding integrated value to produce a plurality of normalized optical density waveforms;

calculating totals of the different lipoprotein components for at least some of the plurality of lipoproteins using the normalized optical density waveforms;

comparing the totals to corresponding reference values; and determining a lipid phenotype based on the comparison of the totals to the corresponding reference values.

10. The method of claim 9, wherein the lipoprotein components are triglyceride and cholesterol.

11. The method of claim 9, wherein the plurality of lipoproteins include high density lipoprotein, low density lipoprotein, very low density lipoprotein, and chylomicron.

12. The method of claim 9, wherein the totals represent total normalized concentrations.

* * * * *